United States Patent [19]
Larnard

[11] Patent Number: 5,421,348
[45] Date of Patent: Jun. 6, 1995

[54] ROTATING GUIDEWIRE EXTENSION SYSTEM WITH MECHANICALLY LOCKING EXTENSION WIRE

[75] Inventor: Donald J. Larnard, Boca Raton, Fla.

[73] Assignee: Cordis Corporation, Miami Lakes, Fla.

[21] Appl. No.: 158,414

[22] Filed: Nov. 29, 1993

[51] Int. Cl.⁶ .............................................. A61B 5/00
[52] U.S. Cl. .................................... 128/772; 128/657
[58] Field of Search ................ 128/657, 772; 604/95, 604/104, 280, 281, 282, 283

[56] References Cited

U.S. PATENT DOCUMENTS

| | | | |
|---|---|---|---|
| 4,757,827 | 7/1988 | Buchbinder et al. | 128/657 X |
| 4,827,941 | 5/1989 | Taylor et al. | |
| 4,875,489 | 10/1989 | Messner et al. | |
| 4,966,163 | 10/1990 | Kraus et al. | 128/772 |
| 5,059,851 | 10/1991 | Corl et al. | 128/657 X |
| 5,113,872 | 5/1992 | Jahrmarkt et al. | |
| 5,117,838 | 6/1992 | Palmer et al. | |
| 5,133,364 | 7/1992 | Palermo et al. | 128/772 |
| 5,163,903 | 11/1992 | Crittenden et al. | |
| 5,197,486 | 3/1993 | Frassica | |
| 5,217,435 | 6/1993 | Kring | 128/772 X |
| 5,234,002 | 8/1993 | Chan | 128/772 |
| 5,234,437 | 8/1993 | Sepetka | 128/772 X |
| 5,243,995 | 9/1993 | Maier | 128/772 |
| 5,267,573 | 12/1993 | Evans et al. | |
| 5,271,415 | 12/1993 | Foerster et al. | 128/772 |
| 5,282,478 | 2/1994 | Fleischhaker, Jr. et al. | |

FOREIGN PATENT DOCUMENTS

674943  8/1990  Switzerland .................. 128/772

Primary Examiner—Sam Rimell
Attorney, Agent, or Firm—Thomas R. Vigil; James P. Hanrath

[57] ABSTRACT

The guidewire extension system includes an initial or primary guidewire having a proximal end having an annular groove structure on an outer surface of the proximal end of the guidewire and an extension guidewire adapted to be releasably but firmly mechanically connected to the proximal end of the initial or primary guidewire. The extension guidewire has a distal end and a proximal end. A connecting assembly, which includes a small diameter tube having a proximal end and a distal end, is mounted at the distal end of the extension guidewire and has a coiled spring received in the tube that is constructed and arranged to receive and grippingly engage and mechanically lock with the annular grooved structure on the outer surface of the proximal end of the initial or primary guidewire in a thread connection. The extension guidewire is disconnected from the initial guidewire by rotating the tube to withdraw the coiled spring from and unthread the coiled spring from the proximal end of the initial or primary guidewire.

18 Claims, 9 Drawing Sheets

ROTATING GUIDEWIRE EXTENSION SYSTEM WITH MECHANICALLY LOCKING EXTENSION WIRE

BACKGROUND OF THE INVENTION

1. Field of the Invention

The present invention relates to a swivelling guidewire extension system including an extension guidewire having a connecting assembly at the distal end thereof for releasably and firmly mechanically connecting with a thread connection to a proximal end of an initially inserted PTCA guidewire having a dilatation balloon catheter positioned thereon and situated within a guiding catheter inserted into a femoral artery or carotid artery, for enabling the dilatation balloon catheter to be removed and replaced with another dilatation balloon catheter.

2. Description of the Related Art Including Information Disclosed Under 37 CFR §§1.97-1.99

Heretofore, it has been proposed to provide an exchange guidewire which, after removal of a shorter initially inserted guidewire, is inserted through a dilatation balloon catheter situated in a guiding catheter inserted in a femoral artery for the purpose of replacing the dilatation balloon catheter.

Since the procedure of utilizing an exchange guidewire is tedious, painstaking, time consuming and has some risk involved, it has also been proposed to utilize a guidewire extension for introducing a new dilatation catheter into a cardiovascular system.

For example, there is proposed in U.K. Patent Application No. 2 180 454 a guidewire system where the proximal end of an initially inserted guidewire is received in a sleeve which is also received over the distal end of an extension wire and the sleeve is crimped to fix the mating ends of the guidewire and extension wire together.

Also, an extendable guidewire system has been proposed in U.S. Pat. No. 4,827,941 wherein a small diameter proximal end portion of a primary or initial guidewire is frictionally received within a tubular member fixed to a distal end of a guidewire extension section.

Further, an extendable guidewire for introducing a dilatation catheter into a cardiovascular system has been proposed in U.S. Pat. No. 4,875,489 where the proximal end of a main guidewire has a tapered end portion which is received into a tubular member having a slit or slot therein which permits it to expand, the tubular member being received within an outer sleeve and fixed to a reduced in diameter distal end of a section of an auxiliary guidewire.

In U.S. Pat. No. 5,113,872 there is disclosed an extension guidewire system which includes an extension guidewire adapted to be releasably but firmly connected to the proximal end of an initial guidewire. The extension guidewire has a distal end and a proximal end, and the system further comprises a connecting assembly mounted at the distal end of the extension guidewire and includes a coiled spring constructed and arranged to receive and grippingly engage and lock against a distal end of the initial guidewire.

In U.S. Pat. No. 5,117,838 there is proposed a guidewire extension system which includes an extension guidewire adapted to be releasably but firmly connected to the proximal end of an initial guidewire. The extension guidewire has a distal end and a proximal end, and the system further comprises a connecting assembly which is mounted at the distal end of the extension guidewire, which includes a coiled spring constructed and arranged to receive and grippingly engage and lock against a distal end of the intial guidewire, and which includes a swivel joint for minimizing, if not eliminating, twisting of the extension guidewire when disconnecting the extension guidewire from the initial guidewire.

Further, a guidewire system for use in catheter exchanges is proposed in U.S. Pat. No. 5,197,486 which connects an extension wire to the proximal end of a guidewire to thereby increase the effective length of the guidewire to permit a catheter exchange. The proximal end of the guidewire is attached to the distal end of the exchange wire by a disconnectable, reattachable connection which avoids deformation of the connected joint. The connection includes a male element in the form of a reduced diameter rod extending axially from the proximal end of the guidewire and a female element attached to the distal end of the extension wire. The female element includes a helical coil receptive to the rod and dimensioned to receive the rod in an interference fit requiring the spring to expand. Separation is effected by imparting a combined twisting and axial separation motion to the guidewire and extension wire.

As will be described in greater detail hereinafter, the guidewire extension system of the present invention provides a simple connecting assembly including a coiled wire spring for quickly and firmly mechanically connecting (locking with a thread connection) the proximal end of an initially inserted guidewire to an extension guidewire and which permits quick and simple disengagement of the initially inserted guidewire from the connecting assembly.

SUMMARY OF THE INVENTION

According to the present invention there is provided a guidewire extension system comprising: an initial or primary guidewire having a proximal end having an annular groove structure on an outer surface of the proximal end of the guidewire, an extension guidewire adapted to be releasably but firmly connected to the proximal end of the initial or primary guidewire, the extension guidewire having a distal end and a proximal end, and a connecting assembly which is mounted at the distal end of the extension guidewire, which includes a coiled spring constructed and arranged to receive and grippingly engage and mechanically lock with the proximal end of the initial or primary guidewire, and which includes a small diameter tube having a proximal end and a distal end, the coiled spring being received in said tube, the distal end of said extension guidewire being received in said proximal end of said tube, the extension guidewire being disconnected from the initial guidewire by rotating the tube to withdraw said coiled spring from and unthread the coiled spring from the proximal end of the initial or primary guidewire.

DESCRIPTION OF THE PREFERRED EMBODIMENTS

Figure 1:
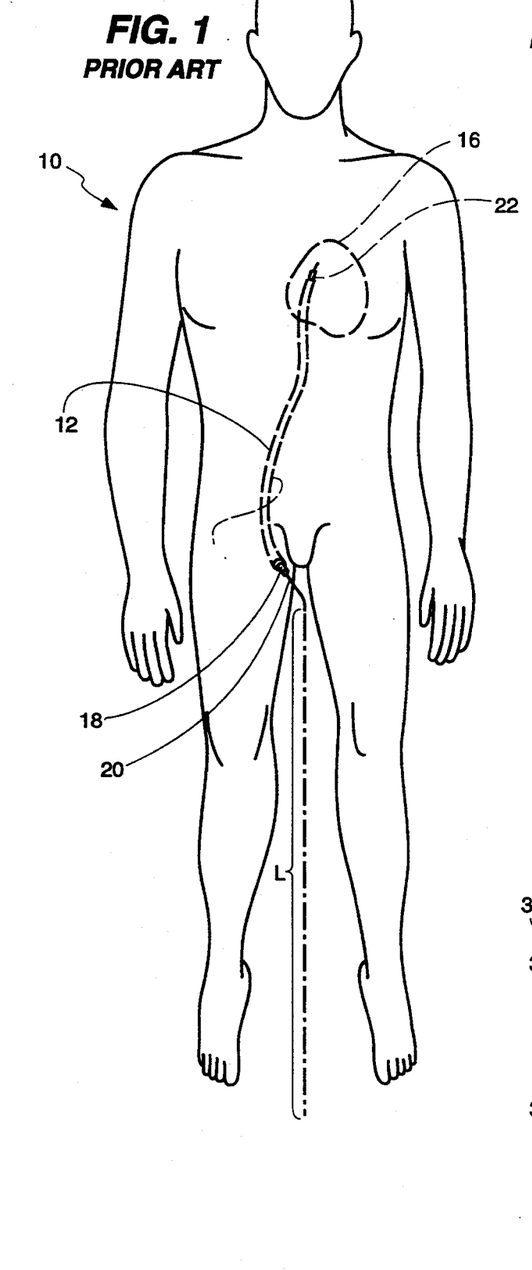
FIG. 1 is a diagrammatic plan view of a patient undergoing catheterization for heart blood vessel angioplasty and shows a catheter inserted percutaneously into and through the femoral artery to the heart, the proximal ends of the catheter and initial guidewire protruding proximally, and shows an extension guidewire.

Referring now to FIG. 1 there is illustrated therein a patient 10 undergoing catheterization for heart angioplasty. For this purpose a guiding catheter 12 had been previously inserted percutaneously into and through the femoral artery 14 into the heart 16. Then a balloon catheter 18 with an initial guidewire 20 therein is inserted through the guiding catheter 12 to place a distal end portion 22 of the balloon catheter 18 and guidewire 20 within the heart.

Figure 2:
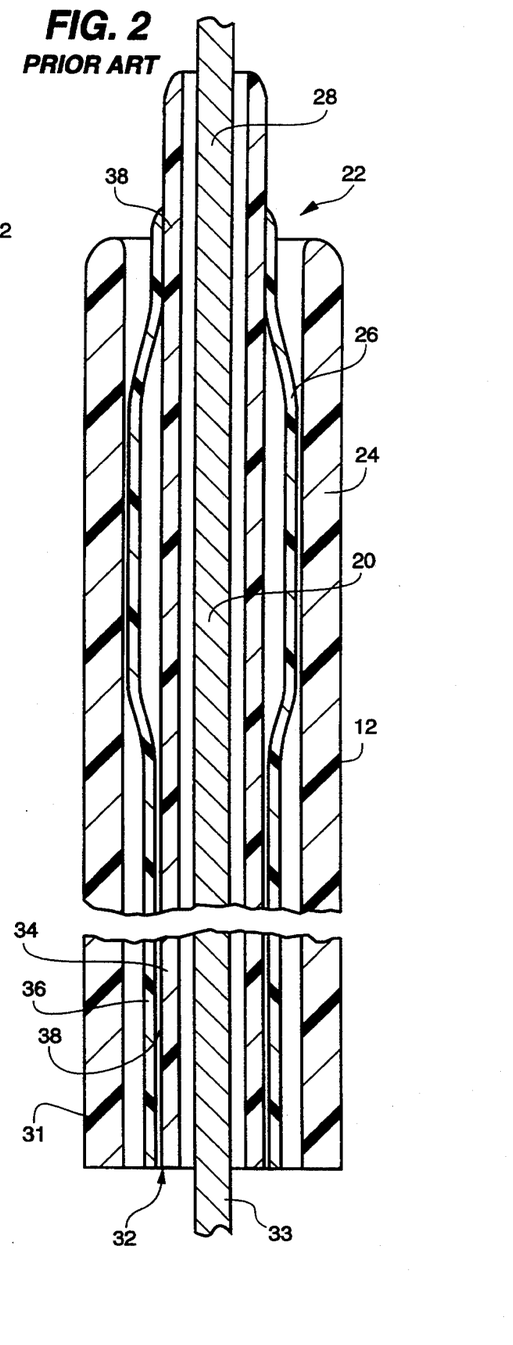
FIG. 2 is an enlarged, longitudinal sectional view of the catheter and guidewire with portions broken away.

An enlarged view of a distal end portion 24 of the guiding catheter 12 having the distal end portion 22 of the balloon catheter 18 with a balloon formation 26, and a distal end 28 of the guidewire 20 therein is shown in FIG. 2. Also shown are the proximal ends 31, 32, 33 of the guiding catheter 12, the balloon catheter 18 and the guidewire 20, respectively. It will be understood that the proximal end 32 of the balloon catheter 18 is connected in a conventional manner to a source of dilatation fluid.

From FIG. 2 it will be seen that the balloon catheter 18 includes a main catheter portion 34 which is received over the initial guidewire, and a balloon catheter portion 36 which is received around and fixed to the main catheter portion 34 adjacent a distal end 38 of the main catheter portion 34. The balloon catheter portion 34 includes the balloon formation 26 in the distal end portion of the balloon catheter 18 as shown.

In use, the distal end portion 22 of the balloon catheter 18 and initial guidewire 20 are moved into an area of stenosis within a blood vessel. Then, a dilatation fluid is supplied through a annular space 38 between the balloon catheter portion 36 and the main catheter portion 34 to the balloon formation 26 for inflating or dilating same thereby to press the stenotic build-up outwardly against the walls of the blood vessel thereby to open the restricted passageway through the stenotic area. Once this has been achieved, the balloon catheter 18 initial guidewire 20 and guiding catheter 12 can be withdrawn or a stent can be implanted in the area of stenosis and then the balloon catheter 18 initial guidewire 20 and guiding catheter 12 are withdrawn.

Often the balloon catheter 18 chosen is the wrong size, the balloon 26 being too small or to large. When this occurs, it is necessary to remove the balloon catheter 18 and replace the same with a new balloon catheter. However, the length of the initial guidewire 20 is such that the whole assembly of balloon catheter 18 and guidewire 20 would have to be removed and replaced with a new balloon catheter and guidewire. This would be a tedious, painstaking and time consuming task, as well as unsafe, and it would be easier if the initial guidewire could be left in place with the initial balloon catheter 18 being removed and then replaced with a new balloon catheter. To enable the old guidewire to be utilized, techniques have been developed for using an exchange guidewire or an extendable guidewire which is capable of being attached and detached from the proximal end of the initially inserted guidewire 20.

It is desirable that the connection or attachment of an extension guidewire be simple and be easily detachable while maintaining a firm attachment or connection between the extension guidewire and the initially inserted guidewire 20.

An extension guidewire 40 and connecting assembly 42 for connecting to the proximal end 33 of the inserted guidewire 20, is shown in FIGS. 3–8.

As shown in FIG. 1 the extension guidewire 40 must have a sufficient length L so that the inserted balloon catheter 18 can be withdrawn over the initially inserted guidewire 20 and the extension guidewire 40 connected thereto and completely out of the guiding catheter 12 and then removed from the extension guidewire 40 so that a new balloon catheter then can be inserted over the extension guidewire 40 and then into the guiding catheter 12 over the initially inserted guidewire 20 to position the balloon 26 thereof in the area of stenosis to be treated.

Figure 3:
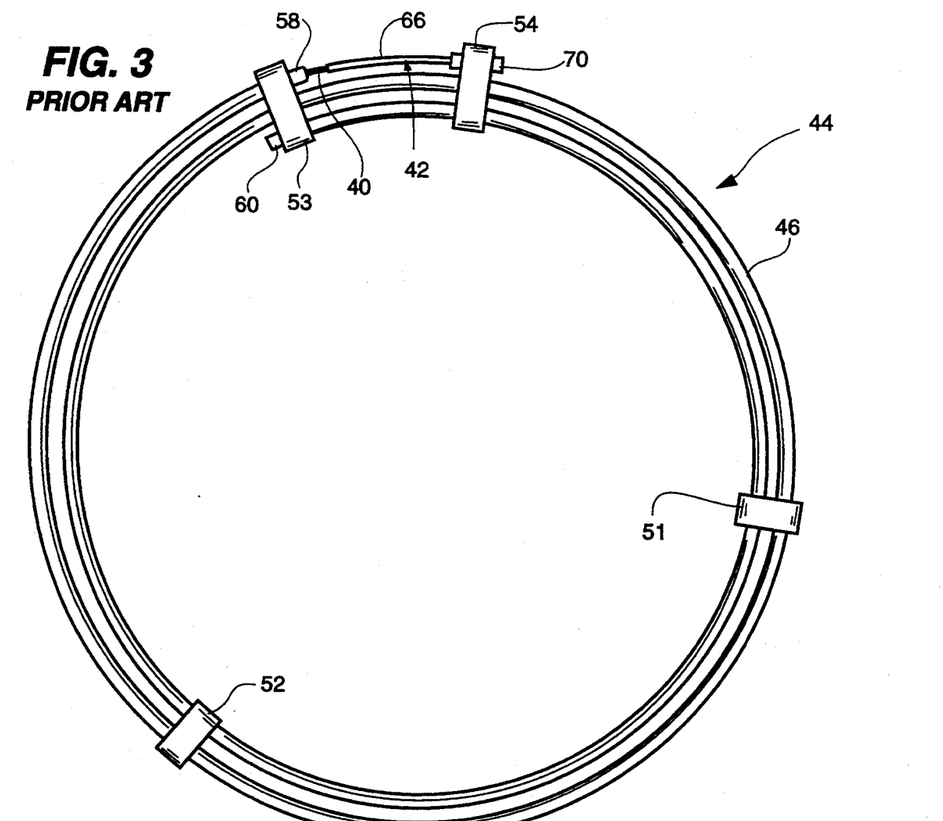
FIG. 3 is a plan view of a coiled plastic tube assembly mounting an extension guidewire constructed according to the teachings of the present invention.
Figure 4:
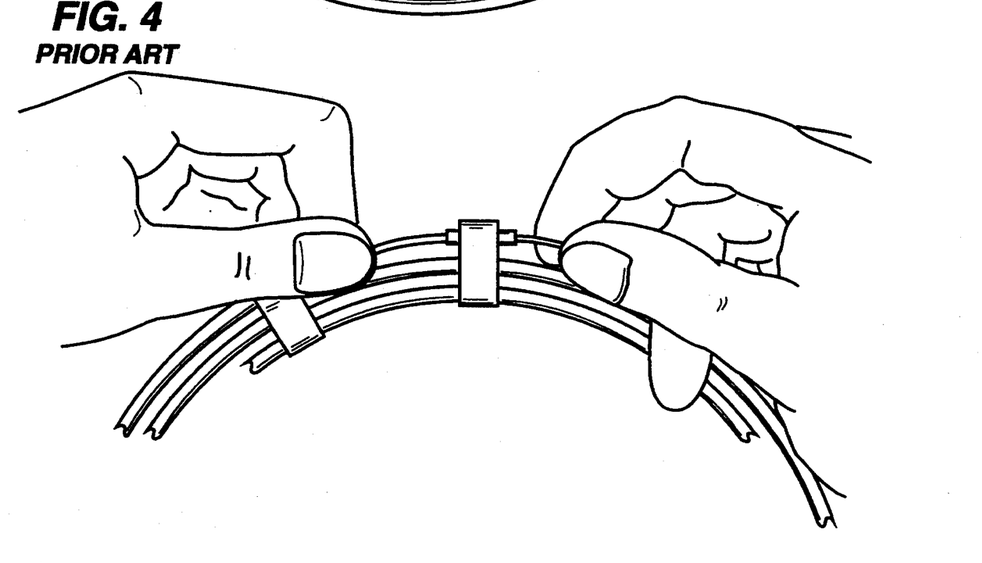
FIG. 4 is a fragmentary plan view of a portion of the coiled tube assembly shown in FIG. 1 and shows a small diameter tube fixed to the distal end of the extension guidewire inserted into a tool situated in an alignment tool holder mounted to the coiled tube assembly and a proximal end of the initial guidewire inserted into the tool for being guided into the small diameter tube.

Referring now to FIG. 3 there is illustrated therein a coiled plastic tube assembly 44 including a coiled plastic tube 46 which is held in a coiled position by four (4) holders 51–54 of the assembly, the holders 51–54 have slots or holes 56 (FIG. 5) therethrough for receiving portions of the coiled tube 46. Two of the holders 51, 52 have two slots/holes 56. On of the holders 53 hold end portions 58, 60 of the coiled tube 46 with a distal end portion 62 of the extension guidewire 40 extending from the open upper or outer end 58 of the coiled tube 46 to and into one of the slots 56 in the holder 54 mounted on the coiled tube 46 a short distance from the holder 53.

Figure 5:
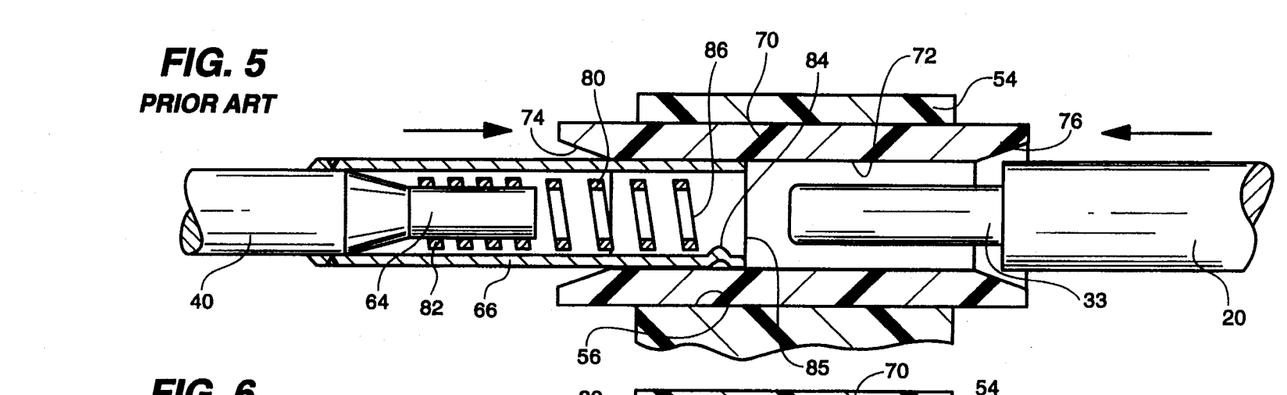
FIG. 5 is an enlarged, longitudinal sectional view of the tool showing the small diameter tubing inserted in the tool and the proximal end of the guidewire positioned for insertion into the tool.

A distal end 64 of the extension guidewire 40 is mounted in a small diameter tube 66, i.e. a tube having the diameter of a hypodermic needle, as shown in FIG. 5. The tube 66 forms part of the connecting assembly 42 mounted to the distal end 64 of the extension guidewire 40.

The tube 66 is received in an alignment tool 70 mounted in one of the slots 46 in the holder 54. The alignment tool 70 is cylindrical in structure and has a cylindrical throughbore 72 which flares or tapers outwardly at each end 74, 76 to facilitate insertion of the small diameter tube 66 in one end 74 and the proximal end 33 of the initial guidewire 20 at the other end 76.

As shown in FIGS. 5–8, inside the small diameter tube 66 of the connecting assembly 42 is an open pitch, flat wire coiled spring 80. Typically the coiled spring 80 has an internal diameter of approximately 0.008 inch and has an inner end 82 which is placed over the ground down distal end 64 of the extension guidewire 40 and welded thereto. The initial guidewire 20 typically has an outer diameter of approximately 0.013–0.014 inch and the proximal end 33 of the initial guidewire 20 is ground down to approximately 0.009 inch.

The tube 66 has a detent or dimple 84 punched therein adjacent an outer end 85 of the tube 66 which engages and prevents an outer end 86 of the spring 80 from being moved out of the tube 66 when the spring 80 is urged out of the tube 66 when the initial guidewire 20 is pulled while the connecting assembly 42 is held against movement.

Figures 6, 7:
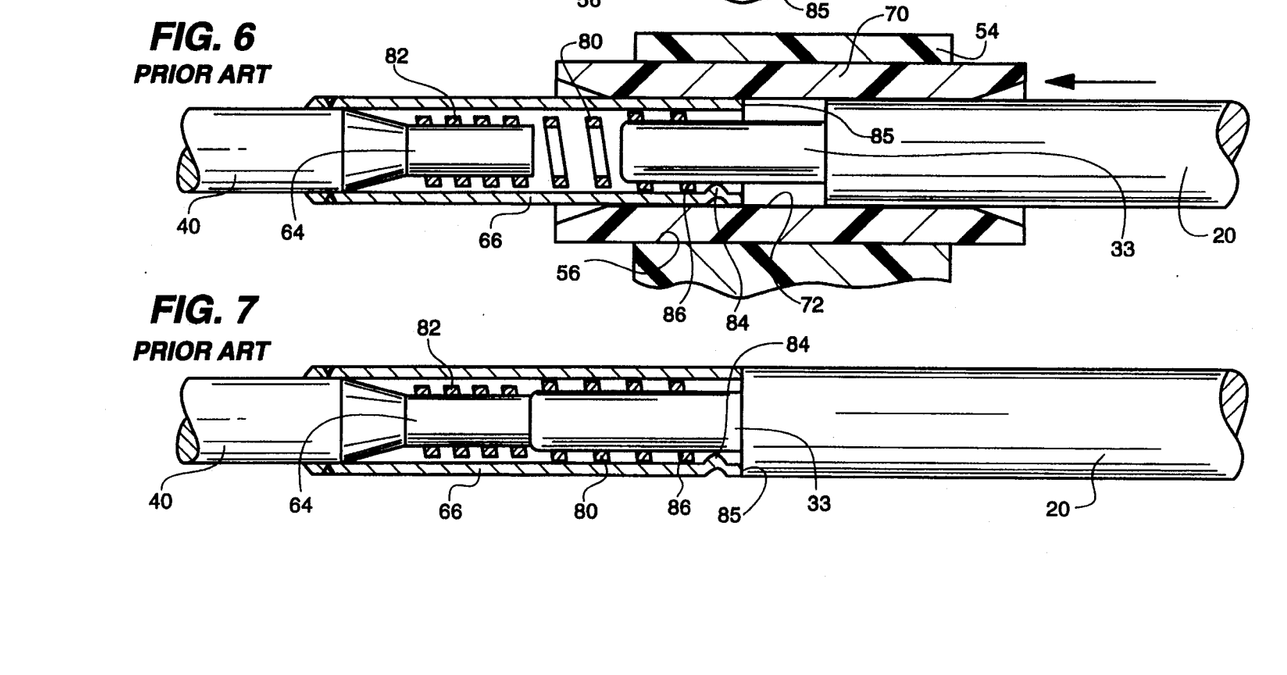
FIG. 6 is an enlarged, longitudinal sectional view of the tool showing the small diameter tubing inserted in the tool, similar to the view shown in FIG. 5 and shows the proximal end of the guidewire inserted into a small coiled spring situated within the small diameter tube and fixed to the distal end of the guidewire extension guideline.
FIG. 7 is an enlarged, longitudinal sectional view of the small diameter tube with the proximal end of the initial guidewire received therein and within the coiled spring.

Referring now to FIGS. 5, 6, and 7, the proximal end 33 of the initial guidewire 20 is inserted into the tool 70 and the proximal end 33 is urged toward the connecting assembly 42 until the proximal end 33 of the initial guidewire 20 engages or bottoms against the distal end 64 of the extension guidewire 40 within the coiled flat wire spring 80. Coils of the flat wire spring 80 then grip or lock against the proximal end 33 of the initial guidewire 40. The above described assembly establishes a secure joint between the distal end 64 of the extension guidewire 40 and the proximal end 33 of the initial guidewire 20.

The coiled tube 46 can then be moved away from this joint to effect removal of the extension guidewire 40 from the coiled tube 46.

Now the implanted "old" balloon catheter 18 can be removed over the extension guidewire 40 and a new balloon catheter can be inserted over the extension guidewire 40 and the initial guidewire 20 to place a new balloon in the stenotic area in a blood vessel.

The extension guidewire 40 and initial guidewire 20 assembly is very effective since, as the proximal end 33 of the initial guidewire 20 is inserted into the coils of the flat wire coiled spring 80, the coils of the coiled spring 80 are forced to uncoil slightly, i.e. move in a direction which establishes a slightly greater inner diameter of the coils, so that the coils can receive therein the outer diameter of the proximal end 33 of the initial guidewire 20. Then, an axial force pulling the proximal end 33 away from the coiled spring 80 causes the coils around the proximal end 33 to tend to move toward a smaller inner diameter and that tendency establishes a locking connection between the coils and the proximal end 33.

If the extension guidewire 40 is pulled, the coiled spring 80 tries to axially extend causing it to try to reduce its internal diameter and this greatly increases the locking force of the flat wire coiled spring 80 against the proximal end 33 of the initial guidewire 20.

Figure 8:
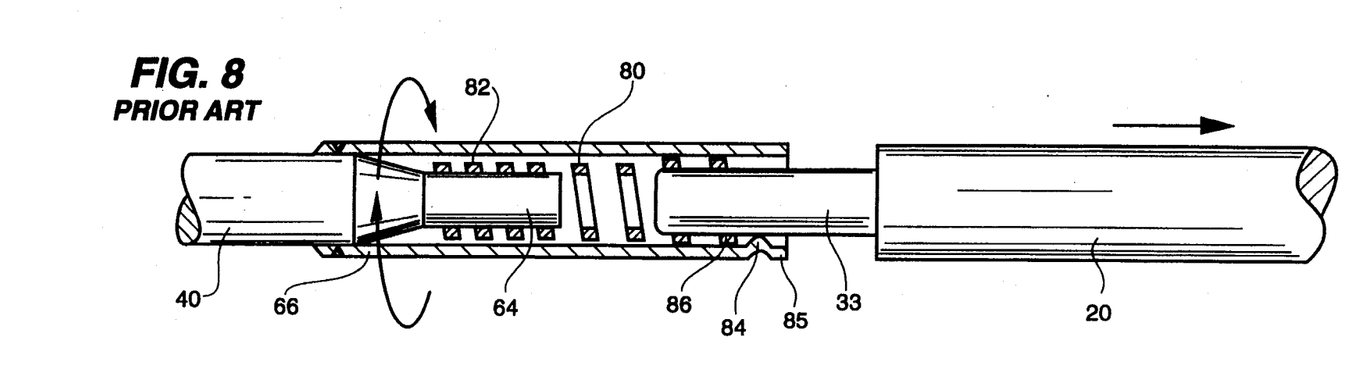
FIG. 8 is an enlarged, longitudinal sectional view of the tube with the small tubing received therein and with the proximal end of the initial guidewire being pulled and simultaneously rotated in a direction which causes expansion of the coiled spring to allow the proximal end of the initial guidewire to be withdrawn from the small diameter tube.

Furthermore, as shown in FIG. 8, it is a simple matter to disengage the extension guidewire 40 from the initial guidewire 20. Disengagement is achieved simply by rotating the extension guidewire 40 to loosen the grip of the spring 80 against the proximal end 33 of the initial guidewire 20 while at the same time pulling the initial guidewire 20 or vice versa to pull the proximal end 33 thereof out of engagement with the coils of the flat wire coiled spring 80 and out of the small diameter tube 66. The detent 84 prevents the outer end 86 of the spring from being pulled out of the tube 66.

The extension guidewire 40 is a flexible 304 stainless steel wire coated with polymerized silicone. The extension guidewire 40 is 125 cm. long and has a diameter of approximately 0.013–0.014 inch. The tube 66 is made of 304 stainless steel and the spring 80 is made of a high tensile strength 304 stainless steel.

With the use of the spring 80 locking against the proximal end 33 of the initial guidewire 20 and the detent 84 blocking movement of the outer end 86 of the spring 80 out of the tube 66, a gripping force is established which would require at least a three pounds axial force to break the connection between the spring 80 and the proximal end 33 of the initial guidewire 20 while allowing the proximal end 33 and the spring 80 to "spin apart" freely. Note that as the spring 80 is pulled axially in a direction out of the tube the coils thereof are urged to a smaller diameter thereby to lock further against the proximal end 33 of the initial guidewire 20 when the initial guidewire 20 is pulled away from the tube 66.

Preferably, the tube 66 is colored a different color than the extension guidewire 40 to facilitate locating of the tube 66 by a medical practitioner.

Further, it is to be understood that the position of the connecting assembly 42 including the tube 66 and the spring 80 can be reversed. That is to say, the connecting assembly 42 can be mounted on the proximal end 30 of the initial guidewire 20 and inserted in the alignment tool 70 to connect with the distal end 64 of the extension guidewire 40.

The coiled tube assembly 44 with extension guidewire 40 therein is packaged in a sterile pouch (not shown) and when used, the following steps are followed:

1. Open the sterile pouch slowly and remove the coiled dispensing tube 46 containing the extension guidewire 40;

2. Insert the proximal end 33 of the primary (initial) guidewire 20 into the alignment tool 70 and gently push the proximal end 33 of the primary or initial guidewire 20 until it is fully seated in the small diameter tube 66;

3. Carefully pull the extension guidewire 40 out of the coiled dispensing tube 46 and alignment tool 70 to prevent it from springing onto a non-sterile field and to prevent kinking of the extension guidewire 40;

CAUTION: Before use, flush all devices entering the vascular system with sterile, heparinized saline or similar isotonic solution.

4. Exchange the dilatation catheters 18 using standard PTCA procedures;

CAUTION: If strong resistance is met during manipulation, discontinue the procedure and determine the cause for the resistance before proceeding.

5. The extension guidewire 40 now can be disengaged from the primary or initial guidewire 20 if desired. This is achieved by holding the proximal end 33 of the primary or initial guidewire 20 while rotating the extension guidewire 40 in a direction so as to expand the spring thereby to loosen the spring and at the same time gently pulling it backwards until it separates from the primary or initial guidewire 20.

It is to be noted that when using the extension guidewire system of the present invention described above, some twisting of the guidewire 40 may be incurred when rotating the connecting assembly 42 to disconnect the initial guidewire 20 from the connecting assembly.

Figure 9:
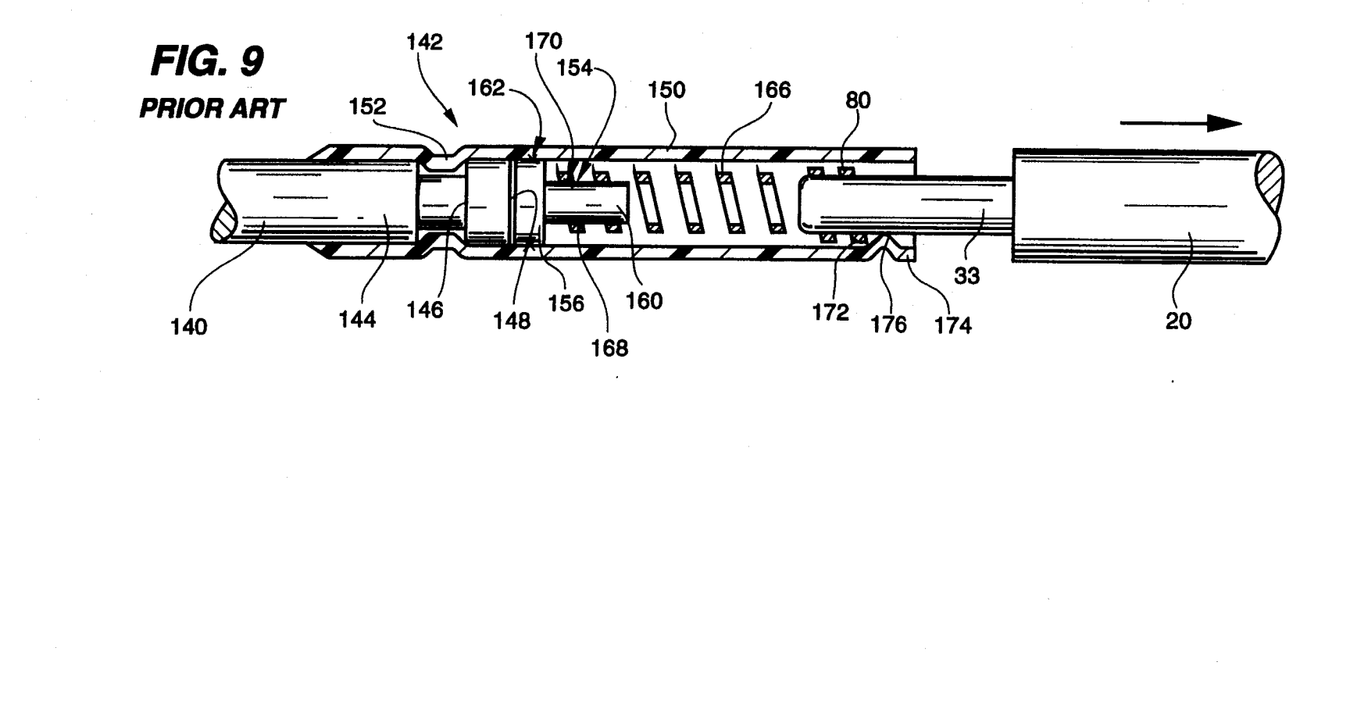
FIG. 9 is an enlarged, longitudinal sectional view of a modified tube having a swivel joint assembly at the proximal end of the tube.

To minimize, if not altogether eliminate, twisting of the guidewire extension 40 when disconnecting the extension guidewire 40 from the initial guidewire 20, a modified extension guidewire 140 and modified connecting assembly 142 can be provided as shown in FIG. 9.

Referring now in greater detail to FIG. 9 there is shown therein a distal end portion 144 of the extension guidewire 140. As shown, the distal end portion 144 has an annular groove 146 cut therein and spaced a short distance from an outer distal end 148 of the extension guidewire 140.

The connecting assembly 142 includes a small diameter tube 150 which is swaged at 152 to form an annular detent which is in registry with the annular groove 146. This construction provides a swivel connection of the extension guidewire 140 to the tube 150 with the annular groove 146 and the annular detent 52 permitting relative rotational movement but not axial movement between the extension guidewire 140 and the tube 150.

As shown, the connecting assembly 142 further includes a step-down piece 154 which includes a disc shaped proximal portion 156 and a reduced-in-diameter distal rod-shaped portion 160. The proximal portion 156 is fixed, such as by weld 162, to the inside of the tube 150.

Then, as in the connecting assembly 142, a flat coiled spring 166 is provided having a proximal end 168 which is fixed, such as by weld 170, to the rod-shaped distal portion 160 of the step-down piece 154 on which it is received.

With this construction, the flat guidewire 166 is fixed to the step-down piece 154 and the step-down piece 154 is fixed to the tube 150 whereby the tube 150 can be rotated to rotate the coiled spring 166 relative to the reduced-in-diameter proximal end portion 33 of the initial guidewire 20.

The coiled spring 166 is identical to the coiled spring 80 of the coupling assembly 42 and has a distal end 172. Then, a distal end portion 174 of the tube 150 has a detent 176 formed therein in the same manner as the detent 84 for the purpose of retaining and holding the coiled spring 166 within the tube 150.

In this embodiment of the extension guidewire system, the connecting assembly 142 can swivel or is rotatable relative to the guidewire 140 so that the guidewire 140 does not have to be twisted when the tube 150 is rotated to cause the coiled flat wire spring 166 to disengage from its gripping engagement with the reduced-in-diameter proximal end 33 of the initial guidewire 20 which then can be pulled, as shown by the arrow in FIG. 9 from the connecting assembly 142 when disengaging the initial guidewire 20 from the extension guidewire 140.

Referring now to FIGS. 10 through 13, there is shown another tool 200 similar to the tool 70 shown in FIGS. 5–7. A small diameter tube 202 of a connecting assembly 204 is received in the tool 200 and has therein an open pitch, flat coiled spring 206. The coiled spring 206 is similar to spring 80 shown in FIGS. 5–7 and has an internal diameter slightly less than the outer diameter of a proximal end 208 of an initial or primary guidewire 210.

However, as illustrated in FIGS. 10 through 13, and according to the teachings of the present invention, the initial or primary guidewire 210 has a proximal end 208 which differs from the previously described guidewire proximal ends by having an annular grooved structure 212 on the outer surface thereof defined by a continuous spiral groove 214. The annular grooved structure 212 on the outer surface of proximal end 208 has a plurality of peaks 216 and valleys 218 which cooperatively correspond to the diameter of the coiled spring 206. In this regard, if the coiled spring 206 has an internal diameter of approximately 0.008 inch, the peaks 216 of the annular groove structure 212 on the outer surface of proximal end 208 of the initial guidewire 210 is ground down to approximately 0.009 inch while the valleys 218 of the annular groove structure 212 on the proximal end 208 on the initial guidewire 210 may correspond to the internal diameter of the coiled spring 206 by being ground down to approximately 0.008 inch. Therefore the indentations (valleys 218) of the annular groove structure 212 on the proximal end 208 match the internal diameter size dimension of the coiled spring 206.

Similar to the embodiment shown in FIGS. 5 through 8, the tube 202 has a detent or dimple 222 punched therein adjacent an outer end 224 of the tube 202 which engages and prevents an outer end 226 of the coiled spring 208 from being moved out of tube 202 when the spring 206 is urged out of the tube 202 when the initial guidewire 210 is pulled when disconnecting the connecting assembly 204 from the proximal end 208.

The coiled spring 206 and the threaded proximal end 208 cooperate with each other to establish a mechanical locking of the extension guidewire to the initial guidewire 210.

Figure 11:
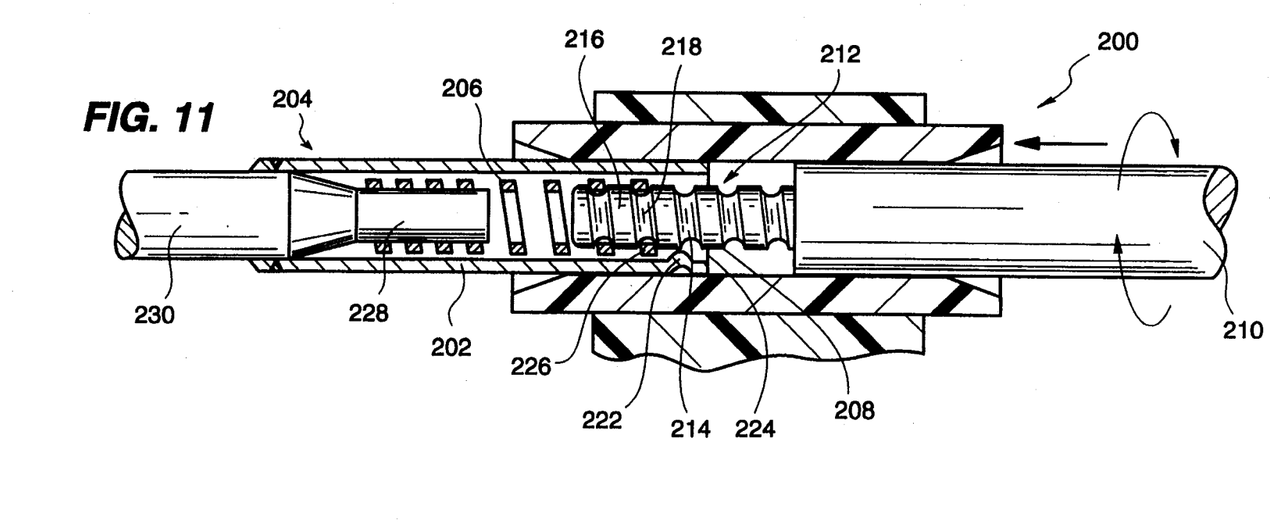
FIG. 11 is an enlarged, longitudinal sectional view of the tool, similar to the view shown in FIG. 10, but showing the alternative proximal end of the guidewire having the threaded outer surface portion partially received, threaded, into a small coiled spring situated within the small diameter tube.
Figure 12:
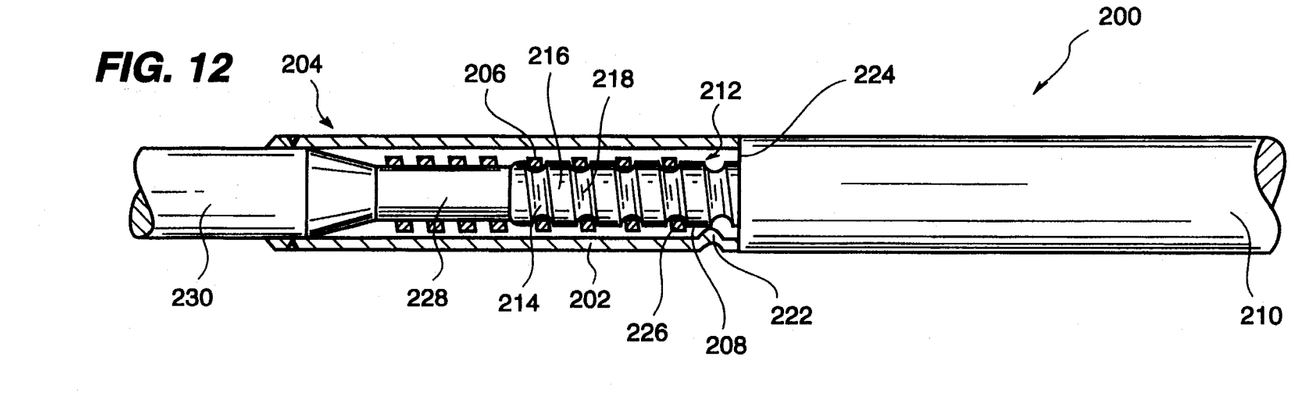
FIG. 12 is an enlarged, longitudinal sectional view of the small diameter tube similar to FIG. 10, but showing the alternative proximal end of the guidewire having the threaded outer surface fully received, threaded, into the coiled spring.

FIGS. 11 and 12 illustrate the connection of the alternative threaded proximal end 208 of the initial guidewire 210 to the connecting assembly 204. The threaded proximal end 208 of the initial guidewire 210 is received into the tube 202 until it engages or bottoms against a distal end 228 of the extension guidewire 230 within the coiled spring 206. A turning of the tube 202 and spring 206 combined with a sliding movement of the proximal end 208 will require the coiled spring 206 to expand and, with a sliding movement of the proximal end 208 within the coiled spring 206, the proximal end 208 is received fully within the coiled spring 206. The coiled spring 206 then resumes a closed position from its previous expanded state such that the inner diameter of the coiled spring 206 seats within the valleys 216 of the annular groove structure 212 on the proximal end 208 of the guidewire 210, thereby not only to receive and grippingly engage the proximal end 208 but also to mechanically lock with the proximal end 208 of the initial or primary guidewire 210 as illustrated in FIG. 12.

The above described assembly establishes a secure joint between the distal end 228 of the extension guidewire 230 and the proximal end 208 of the initial or primary guidewire 210 which will withstand substantial separation forces without disconnecting.

It is preferable that the coiled spring 206 comprises a circular cross section wire as opposed to a flat wire as the circular cross section wire will better seat within the valleys 216 of the annular groove structure 212 on the proximal end 208 of the guidewire 210.

Figure 13:
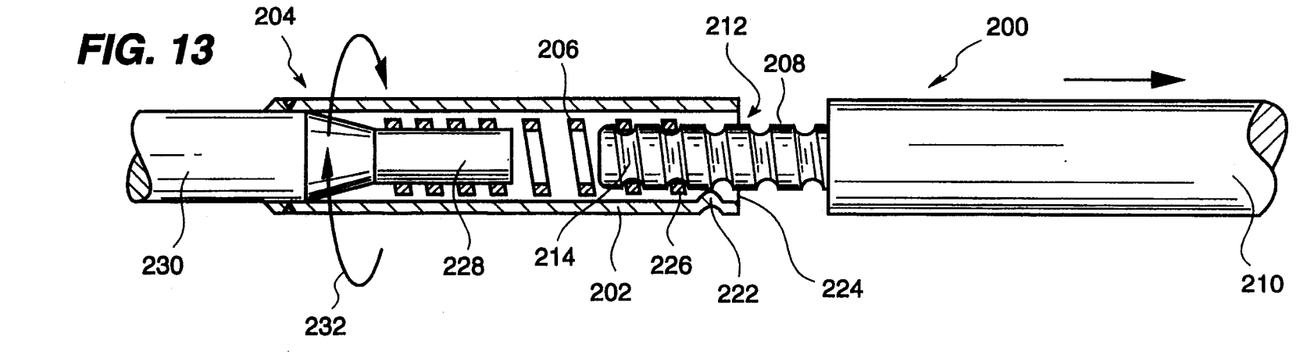
FIG. 13 is an enlarged, longitudinal sectional view of the tube similar to the view shown in FIG. 10 but showing the proximal end being withdrawn from the tube and simultaneously rotated in a direction which causes expansion of the coiled spring to allow the alternative proximal end of the guidewire to be unthreaded/withdrawn from the small diameter tube.

FIG. 13 illustrates how the tube 202 can be moved away from the joined position illustrated at FIG. 12 to effect removal of the initial guidewire 210 from the tube 202. In this regard, a twisting of tube 202 in a direction counter to the direction of the coiled spring 206 winding (see directional arrow 232) and a simultaneous pulling away of the proximal end 208 of the initial or primary guidewire 210 will expand the coiled spring 206 and break the mechanical lock of the coiled spring 206 upon the threaded proximal end 208 thus permitting the two to be axially separated and the threaded proximal end 208 of the initial guidewire 210 to be withdrawn from the small diameter tube 202.

Another embodiment of a modified proximal end of a primary guidewire is shown in FIGS. 14–17.

Figure 10:
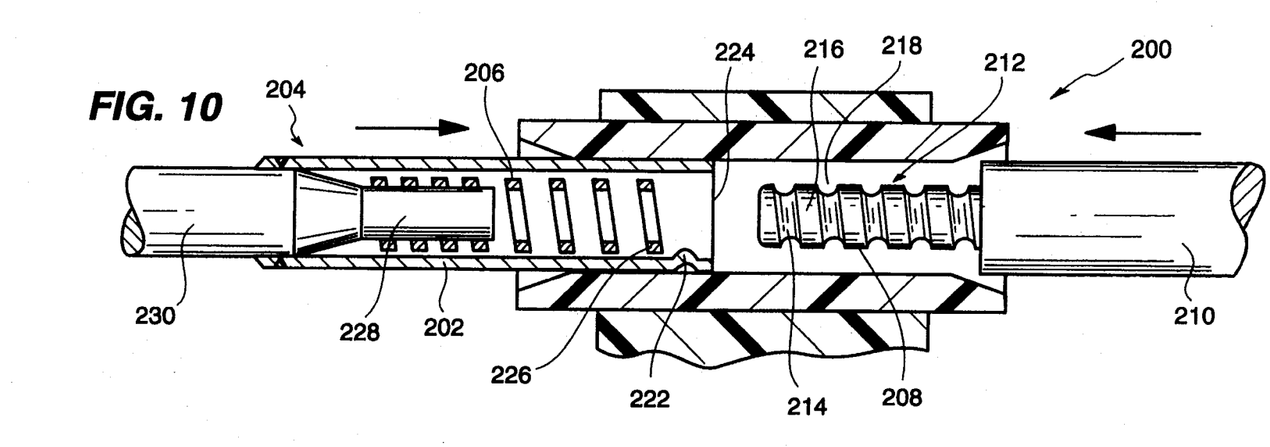
FIG. 10 is an enlarged, longitudinal sectional view of the tool with the small diameter tubing inserted into one end of the tool and an alternative proximal end of the initial or primary guidewire having an annular groove structure on the outer surface thereof defined by a continuous spiral groove forming a threaded outer surface inserted into the other end of the tool.
Figure 14:
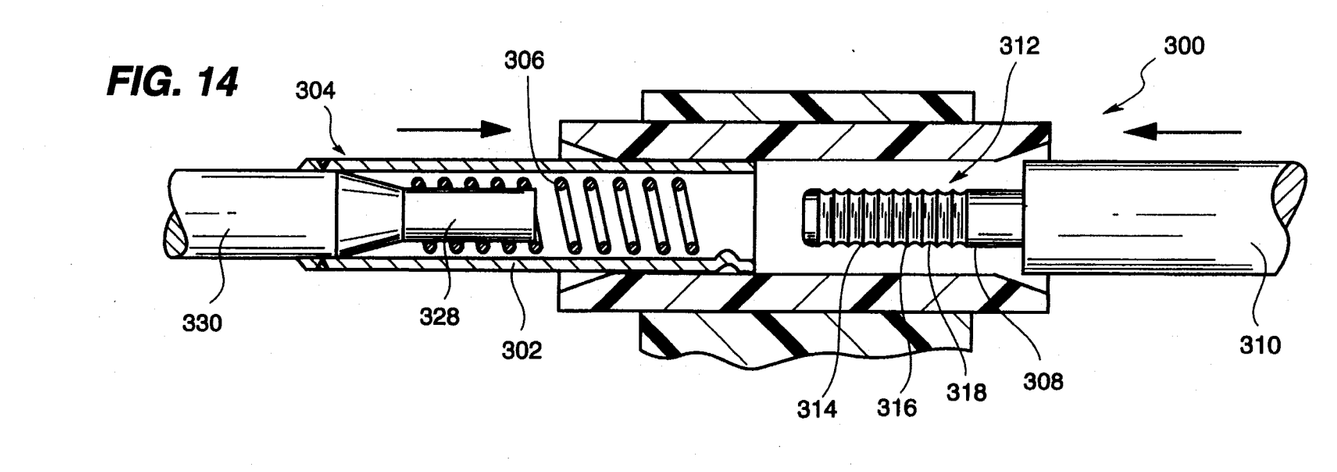
FIG. 14 is an enlarged, longitudinal sectional view of the tool with the small diameter tubing inserted into one end of the tool and another alternative embodiment of a proximal end of the initial or primary guidewire having an annular groove structure on the outer surface thereof defined by a plurality of spaced apart grooves forming a serrated outer surface inserted into the other end of the tool.

Here a tool 300, similar in structure and function to the tool 200 shown in FIG. 10, is shown with a tube 302 of a connecting assembly 304 therein. A coiled spring 306 is mounted within the tube 302. In this embodiment, a proximal end 308 of an initial guidewire 310 has an annular groove structure 312 on the outer surface thereof defined by a plurality of spaced apart annular grooves 314 providing a serrated outer surface on the proximal end 308 of the initial or primary guidewire 310.

The coiled spring 306 is similar to the coiled spring 206 shown in FIG. 10 and has an internal diameter slightly less than the outer diameter of the serrated proximal end 308 of the initial or primary guidewire 310. The annular groove structure 312 on the serrated proximal end 308 has a plurality of peaks 316 and valleys 318 which cooperatively correspond to the diameter of the coiled spring 306.

Figure 15:
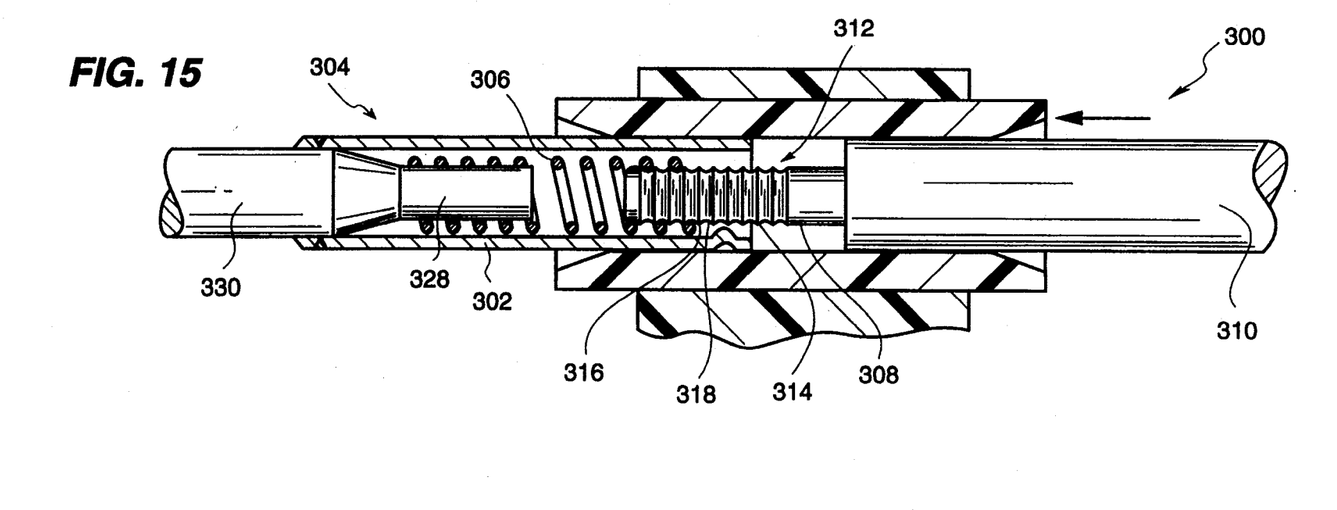
FIG. 15 is an enlarged, longitudinal sectional view of the tool similar to the view shown in FIG. 14, but showing the alternative proximal end of the guidewire having the serrated outer surface partially received, threaded, into a small coiled spring situated within the small diameter tube.

The coiled spring 306 and the serrated proximal end 308 cooperate with each other to establish a mechanical locking of a distal end 328 of an extension guidewire 330. FIGS. 14 and 15 illustrate the connection of the alternative serrated proximal end 308 of the initial guidewire 310 having an annular groove structure 312 defined by a plurality of spaced apart annular grooves 314 to the connecting assembly 304 until the serrated proximal end 308 of the initial guidewire 310 engages or bottoms against the distal end 328 of the extension guidewire 330 within the coiled spring 306. A turning, combined with a sliding movement of the serrated proximal end 308 will force the coiled spring 306 to expand permitting a sliding movement of the serrated proximal end 308 into the coiled spring 306 to fully receive the serrated proximal end 308 into the coiled spring 306.

Figure 16:
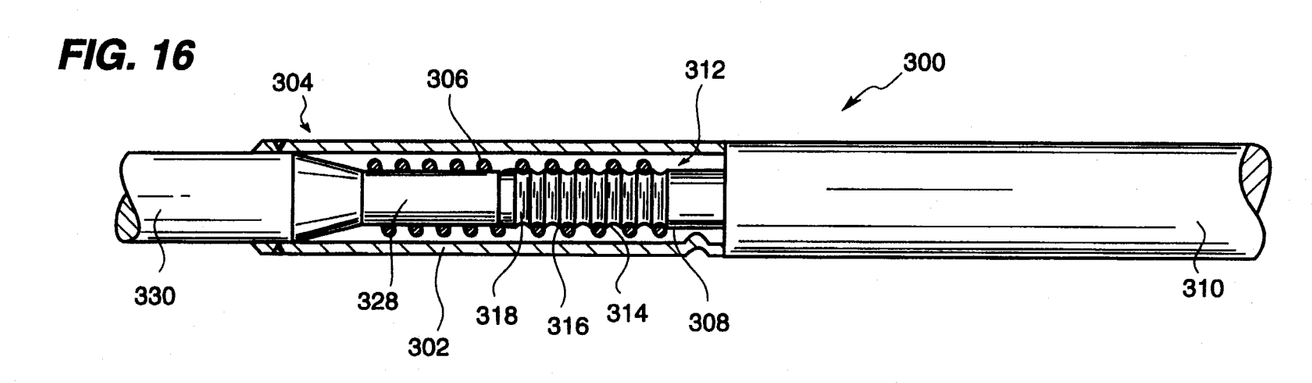
FIG. 16 is an enlarged, longitudinal sectional view of the small diameter tube similar to the view shown in FIG. 14, but showing the alternative proximal end of the guidewire having the serrated outer surface fully received, threaded, into the coiled spring.

FIG. 16 shows that once the serrated proximal end 308 is fully received within the coiled spring 306, the coiled spring 306 will resume a closed position, from its previous expanded state, such that portions of the inner diameter of the coiled spring 306 seats within the valleys 316 of the annular groove structure 312 on the serrated proximal end 308 of the guidewire 310 thereby not only to receive and grippingly engage the proximal end 308, but also to accomplish a secure mechanical lock with the proximal end 308 of the initial or primary guidewire 310 which will withstand substantial separation forces without disconnecting.

Figure 17:
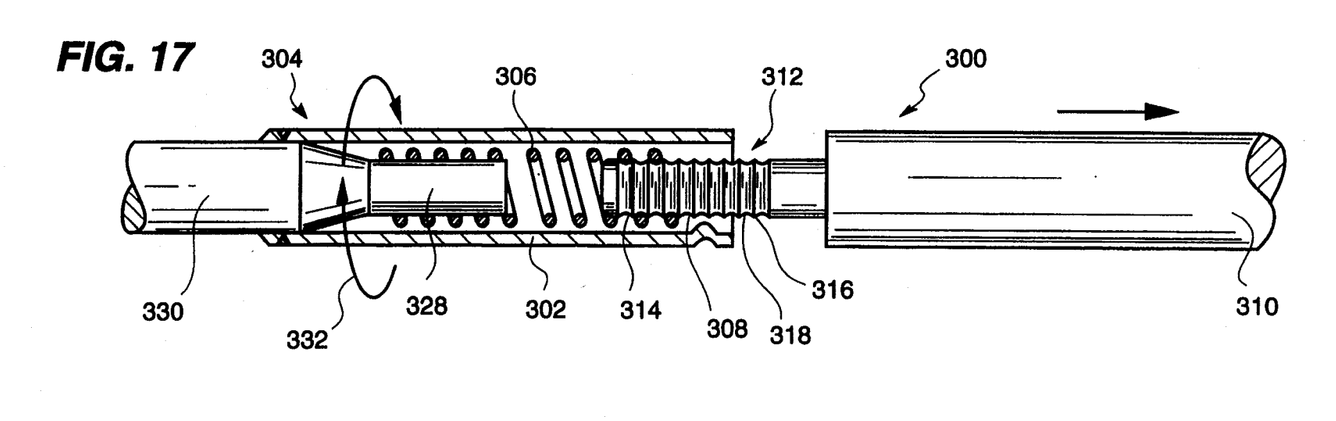
FIG. 17 is an enlarged, longitudinal sectional view of the tube, similar to the view shown in FIG. 14, but showing the proximal end being withdrawn from the tube and simultaneously rotated in a direction which causes expansion of the coiled spring to allow the alternative proximal end of the guidewire to be unthreaded/withdrawn from the small diameter tube.

FIG. 17 illustrates the disconnecting of the tube 302 away from the joined position illustrated in FIG. 16 to effect removal of the initial guidewire 310 from the tube 302. A twisting of tube 302 in a direction counter to the direction of the coiled spring 306 winding (see directional arrow 332) and simultaneous pulling away of the proximal end 308 of the initial or primary guidewire 310 will expand the coiled spring 306 and break the mechanical lock of the coiled spring 306 upon the serrated proximal end 308 thus permitting the two to be axially separated and the serrated proximal end 308 of the initial guidewire 310 to be withdrawn from the small diameter tube 302.

The extendable guidewire system including the connecting assembly 204 or 304 and the annular groove structure 212 or 312 on the proximal end 208 or 308 of the primary guidewire 210 or 310 of the present invention has a number of advantages some of which have been described above and others of which are inherent in the system. Additionally, modifications can be made to the extension guidewire system without departing from the teachings of the present invention; for example, the coiled spring 206 or 306 can be round instead of flat. Accordingly, the scope of the invention is only to be limited as necessitated by the accompanying claims.

We claim:

1. A guidewire extension system comprising: an initial guidewire having a proximal end portion having an annular groove structure on an outer surface of said proximal end portion, an extension guidewire adapted to be releasably but firmly connected to said proximal end portion of said initial guidewire, said extension guidewire having a distal end portion including a distal end and having a proximal end, and a connecting assembly which is mounted on said distal end portion of said extension guidewire, which includes a coiled spring constructed and arranged to receive and grippingly engage and mechanically lock with said proximal end of said initial guidewire, and which includes a small diameter tube of the type used for a hypodermic needle and commonly referred to as a hypo tube, said tube having a proximal end and a distal end, said coiled spring being received loosely in said tube with an inner end of said coiled spring fixed in said tube and the remainder of the coiled spring not being in fixed engagement with an interior wall of said tube, said distal end of said extension guidewire being received in said proximal end of said tube, said extension guidewire being disconnected from said initial guidewire by rotating said tube to withdraw said coiled spring from and unthread said coiled spring from said proximal end portion of said initial guidewire.

2. The guidewire extension system of claim 1 wherein said annular groove structure on said outer surface of said proximal end portion of said initial guidewire is defined by a continuous spiral groove forming a thread on said proximal end portion of said initial guidewire.

3. The guidewire extension system of claim 1 wherein said annular groove structure on the outer surface of said proximal end portion of said initial guidewire is defined by a plurality of spaced apart annular grooves forming a serrated surface on said proximal end portion of said initial guidewire.

4. The guidewire extension system of claim 1 wherein said connecting assembly includes said distal end portion of said extension guidewire which has a proximal portion and a reduced in cross-section distal portion, said small diameter tube is received over said coiled spring and said distal end portion of said extension guidewire, said proximal portion of said distal end portion of said extension guidewire being fixed to said tube and said coiled spring being fixed to said distal portion of said distal end portion of said extension guidewire.

5. The guidewire extension system of claim 1 wherein said proximal portion of said distal end portion of said extension guidewire has an annular groove therein and said proximal end of said tube received over said distal end portion has a swaged down annular detent which is in registry with said annular groove in a manner which permits relative rotational movement, but no axial movement between said extension guidewire and said tube.

6. The guidewire extension system of claim 1 wherein said coiled spring comprises an open pitch wire coiled spring having an internal diameter slightly less than the outer diameter of said proximal end of the initial guidewire so that, when the coiled spring is urged toward said proximal end, the coils of said coiled spring are caused to thread upon said annular groove structure on the outer surface of said proximal end of the initial guidewire to receive the proximal end therein and when said coiled spring is urged from said proximal end, the coils of said coiled spring are caused to unthread from said annular groove structure on the outer surface of said proximal end of the initial guidewire.

7. The guidewire extension system of claim 1 wherein said tube has a detent punched therein adjacent the outer end of the tube for engaging and preventing the outer end of the coiled spring from being moved out of the tube when the proximal end of the initial guidewire is urged out of the tube.

8. The guidewire extension system of claim 1 wherein said coiled spring comprises an open pitch wire coiled spring having an internal diameter cooperatively corresponding to said annular groove structure on the outer surface of the proximal end portion of said initial guidewire so that, when the coiled spring is urged toward said proximal end, the coils of said coiled spring are caused to thread upon said annular groove structure on the outer surface of said proximal end portion of said initial guidewire to receive the proximal end portion therein, a proximal end of said coiled spring is fixed to said distal end portion of said extension wire inside and fixed to said small diameter tube, and said tube which is received over said coiled spring has a detent punched therein adjacent the outer end of the tube for engaging and preventing the outer end of the coiled spring from being moved out of the tube when the proximal end of the initial guidewire is urged out of the tube, the coils of said coiled spring being capable of a threaded engagement with the proximal end of the initial guidewire, thereby causing the coils of said coiled spring to mechanically lock with said proximal end portion, and the locking force of said coils against the proximal end and the blocking force of said detent against a distal coil of said coiled spring, requires a rotatable force to free the proximal end from the connecting assembly.

9. The guidewire extension system of claim 1 wherein said tube is colored a different color than said extension guidewire to facilitate the locating of the tube.

10. The guidewire extension system of claim 1 further comprising an alignment tool which includes a body having a cylindrical passageway therethrough into one end of which the connecting assembly is inserted and into the other end of which is inserted the proximal end of the initial guidewire for being guided in an aligned manner into said connecting assembly.

11. The guidewire extension system of claim 9 wherein said cylindrical passageway in said alignment tool is flared or tapered radially outwardly at each end thereof to facilitate insertion of the connecting assembly in one end and the proximal end of the initial guidewire in the other end.

12. The guidewire extension system of claim 1 combined with a coiled tube assembly including a coiled plastic dispensing tube in which the extension guidewire is received and stored in a sterile manner.

13. The guidewire extension system of claim 12 further comprising an alignment tool which includes a body having a cylindrical passageway therethrough into one end of which the connecting assembly is inserted and into the other end of which is inserted the proximal end of the initial guidewire for being guided in an aligned manner into said connecting assembly, said alignment tool being mounted to said coiled dispensing tube adjacent an outlet end of said coiled tube.

14. A guidewire extension system for coupling a distal end portion of an extension guidewire to a proximal end portion of an initial guidewire, said system comprising a rotatable connecting assembly mounted to one of:
(a) the distal end portion of the extension guidewire or
(b) the proximal end portion of the initial guidewire and including a small diameter tube of the type used for a hypodermic needle and commonly referred to as a hypo tube and a coiled spring having an inner end thereof fixed in said tube with the remainder of said coiled spring not being fixed to an interior wall of said tube and said coiled spring being constructed and arranged to thread upon an annular groove structure on the outer surface of one of: (b) the proximal end portion of the initial guidewire or (a) the distal end portion of the extension guidewire.

15. A method for connecting an extension guidewire to an initial guidewire, said method comprising the steps of:

providing an initial guidewire having a proximal end portion;

providing a length of extension guidewire having a distal end portion;

providing a rotatable connecting assembly on one of (a) the distal end portion of the extension guidewire or the proximal end portion of the initial guidewire;

providing an annular groove structure on an outer surface of one of (b) the proximal end portion of the initial guidewire or (a) the distal end portion of the extension guidewire;

providing the rotatable connecting assembly with a small diameter tube of the type used for a hypodermic needle and commonly referred to as a hypo tube and a coiled spring having an inner end fixed in the tube with the remainder of said tube being loose in said tube and not fixed to an interior wall of said tube and arranging said coiled tube to be received upon and mechanically lock with an end portion of one of said guidewires having said annular groove structure; and, axially inserting into the connecting assembly and within the coiled spring one of (b) the proximal end portion of the initial guidewire or (a) the distal end portion of the extension guidewire, thereby to connect firmly the distal end portion of the extension guidewire to the proximal end portion of the initial guidewire.

16. The method of claim 15 including the further step of removing the extension guidewire by pulling the proximal end portion of the initial guidewire away from the coiled spring while simultaneously rotating the tube of the connecting assembly rotatably journaled on the distal end portion of the extension guidewire in a direction which unthreads the spring from the proximal end portion of the initial guidewire.

17. A method of replacing an initial dilatation balloon catheter previously inserted with and over an initial guidewire and through a guiding catheter into a vascular system comprising the steps of:

performing the method steps defined in claim 15;

removing the initial dilatation balloon catheter over the extension guidewire; and inserting a new dilatation balloon catheter over the extension guidewire and the initial guidewire and positioning the balloon thereof at approximately the same location where the balloon of the initial dilatation balloon catheter had been located.

18. The method of claim 17 including the further step of removing the extension guidewire by pulling the proximal end of the initial guidewire away from the coiled spring while simultaneously rotating the tube of the connecting assembly rotatably journaled on the distal end of the extension guidewire in a direction which unthreads the spring from the proximal end of the initial guidewire.

* * * * *